United States Patent
Parady et al.

(10) Patent No.: US 6,441,235 B1
(45) Date of Patent: Aug. 27, 2002

(54) PREPARATION OF 5-AMINO-ISOPHTHALAMIDES

(75) Inventors: Edward David Parady, Castleton, NY (US); Karl Olaf Gelotte, Watchung, NJ (US)

(73) Assignee: Amersha, Health AS, Oslo (NO)

( * ) Notice: Subject to any disclaimer, the term of this patent is extended or adjusted under 35 U.S.C. 154(b) by 0 days.

(21) Appl. No.: 09/855,124

(22) Filed: May 14, 2001
(Under 37 CFR 1.47)

Related U.S. Application Data

(63) Continuation of application No. PCT/GB99/03795, filed on Nov. 15, 1999.
(60) Provisional application No. 60/108,613, filed on Nov. 16, 1998.

(30) Foreign Application Priority Data

Nov. 16, 1998 (GB) ............................................. 9825095

(51) Int. Cl.⁷ ...................... C07C 231/02; C07C 233/05
(52) U.S. Cl. ........................ 564/157; 564/139; 564/416; 564/418
(58) Field of Search ................................. 564/139, 157, 564/416, 418

(56) References Cited

U.S. PATENT DOCUMENTS

| 4,001,323 A | | 1/1977 | Felder et al. | |
| 4,256,729 A | * | 3/1981 | Lin | ............................... 424/5 |

FOREIGN PATENT DOCUMENTS

| EP | 1186305 | * | 3/2002 |
| GB | 1 548 594 | | 7/1979 |

* cited by examiner

Primary Examiner—Shailendra Kumar
(74) Attorney, Agent, or Firm—Royal N. Ronning, Jr.; Robert F. Chisholm; Stephen G. Ryan

(57) ABSTRACT

A process for preparing 5-amino-N,N'-bis(R) isophthalamides, where A is 2,3-dihydroxypropyl or 1,3-dihydroxyisopropyl, useful as intermediates in preparing iodinated diagnostic agents, which comprises reacting a di-lower-alkyl 5-nitroisophthalate with a compound of the formula $RNH_2$ in the presence of a basic catalyst and without isolating the intermediate 5-nitro-N,N'-bis(R) isophthalamide, catalytically hydrogenating the latter.

7 Claims, No Drawings

PREPARATION OF 5-AMINO-ISOPHTHALAMIDES

This application is a continuation of PCT/GB99/03795, filed Nov. 15, 1999 (of which the entire disclosure of the pending, prior application is hereby incorporated by reference), which itself is a continuation-in-part of application Ser. No. 60/108,613, filed Nov. 16, 1998.

BACKGROUND OF THE INVENTION

1. Field of the Invention

The process relates to an improved method of preparing 5-amino-N,N'-bis(R)isophthalamides, where R is 2,3-dihydroxy propyl or 1,3-dihydroxyisopropyl, which compounds are useful as intermediates in preparing iodinated diagnostic agents.

2. Description of the Prior Art

Nyegaard & Co. British Patent 1,548,594, published Jul. 18, 1979 describes a process for preparing 5-amino-N,N'-bis(2,3-dihydroxypropyl)isophthalamide as follows:

Dimethyl 5-nitro-isophthalate and 2.4 molar equivalents of 1-amino-2,3-propanediol were refluxed in methanol for twenty hours and the resulting 5-nitro-N,N'-bis(2,3-dihydroxypropyl)isophthalamide was isolated in 84% yield. The latter compound was suspended in aqueous hydrochloric acid and hydrogenated in the presence of a palladium oxide/charcoal catalyst. The resulting 5-amino-N,N'-bis(2,3-dihydroxypropyl)-isophthalamide was not isolated but the acid solution containing it was iodinated with sodium iodine dichloride to obtain 5-amino-2,4,6-triiodo- N,N'-bis(2,3-dihydroxypropyl)isophthalamide in 71% yield from the nitro compound (over-all yield of 59.5% from dimethyl 5-nitroisophthalate). Subsequent reactions are described for the preparation of 5-[N-(2,3-dihydroxy-propyl)acetamido]-2,4,6 triiodo-N,N'-bis(2,3-dihydroxypropyl)isophthalamide, useful as an X-ray contrast agent.

Felder et al. U.S. Pat. No. 4,001,323, issued Jan. 4, 1977 describes (Example 7) the reaction of 47.9 g. (0.2 mole) of dimethyl 5-nitroisophthalate and 22.8 g. (0.25 mole) of 1,3-dihydroxyisopropylamine (serinol), 5 hours at 140–150° C. and the isolation of 57.2 g. of 5-nitroisophthalic acid di(1,3-dihydroxypropylamide). This represents an apparent 80% yield based on the starting ester; however it is stoichiometrically impossible to obtain this amount of product in view of the deficiency in the amount of serinol since the reaction requires two moles of amine for every mole of ester. Felder et al. further describe the hydrogenation of the nitro bis-amide in ethanol solution in the presence of palladium-carbon catalyst and iodination of the resulting 5-aminoisophthalic acid di(1,3-dihydroxy-propylamide) in 75% over-all yield.

SUMMARY OF THE INVENTION

The invention relates to an improvement in the preparation of a compound of the formula

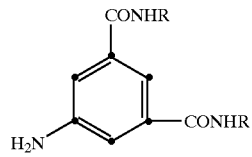

where R is $CH_2CH(OH)CH_2OH$ or $CH(CH_2OH)_2$, which comprises reacting a di-lower-alkyl 5-nitroisophthalate with at least two molar equivalents of a compound of the formula $RNH_2$ in a solvent comprising a lower-aliphatic alcohol containing a basic catalyst to obtain a solution containing 5-nitro-N,N'-bis(R)isophthalamide, and, without isolating the latter, catalytically hydrogenating said solution to obtain a solution of 5- amino-N,N'-bis(R)-isophthalamide.

DETAILED DESCRIPTION INCLUSIVE OF PREFERRED EMBODIMENTS

The starting material for the process of the invention is a di-lower-alkyl 5-nitroisophthalate wherein lower-alkyl preferably has from one to four carbon atoms. The conversion of the di-lower-alkyl 5-nitroisophthalate to 5-nitro-N,N'-bis(R)-isophthalamide takes place in a solvent comprising a lower-aliphatic alcohol containing a basic catalyst. The lower-aliphatic alcohol solvent is preferably a lower-alkanol or lower-alkoxyalkanol of one to four carbon atoms, for example, methanol, ethanol, 1-propanol, 2-propanol, 1-butanol, 2-butanol, 2-methoxyethanol, 2-ethoxyethanol or 3-methoxypropanol. The basic catalyst is a strong base preferably derived from the addition of an alkali metal to the lower-aliphatic alcohol solvent. The amide formation is carried out at a temperature between about 65 and 150° C. depending upon the solvent used and conveniently at approximately the boiling point of the solvent, and the reaction is complete in a few hours.

The amine reactant, $H_2NCH_2CH(OH)CH_2OH$, has an asymmetric carbon atom and thus exists in the racemic form and in its optically active dextro or levo forms. The process of the invention can be carried out with either the racemic form or one of the optically active forms.

No isolation of the intermediate 5-nitro-N,N'-bis(R)-isophthalamide is effected, and the solution thereof is directly hydrogenated in the presence of a catalyst effective in the reduction of aromatic nitro groups to amino groups. Exemplary of such catalysts are platinum or palladium or the oxides thereof, preferably supported on carbon. The hydrogenation reaction can be initiated at room temperature or above. Hydrogenation is complete in about one hour's time. The resulting 5-amino-N,N'-bis(R)isophthalamide can be isolated in the free base form by filtering off the catalyst and removing the solvent by evaporation or distillation; or in the form of an acid-addition salt by the addition of a strong inorganic or organic acid to the product solution whereby the respective acid-addition salt separates in crystalline form from the solution. Appropriate acid-addition salts are the hydrochloride, hydrobromide, methanesulfonate and the like.

The process of the instant invention possesses several distinct advantages over the processes disclosed in the prior art. The process disclosed and claimed herein can be carried out on a large scale in yield of 96.9–99.6%. This represents an improvement of 13–15% in yield over that (84%) described in British Patent 1,548,594 even assuming a quantitative yield in the catalytic hydrogenation reaction of the reference patent. Furthermore, the instant process can be carried out in a period of five hours effective reaction time as compared with 44 hours in the process of the British patent (20 hours for the amidation and one day for the hydrogenation). Finally, it has been found possible to use only a 5% excess of expensive 2,3-dihydroxypropyl-amine to obtain a nearly quantitative yield of product by the instant process as compared to a 20% excess in the process of the British patent.

The following examples will illustrate the invention without the latter being limited thereby.

EXAMPLE 1

Dimethyl 5-nitroisophthalate (23.9 g., 0.100 mole) was slurried in 100 ml. of 2-methoxyethanol and 19.1 g. (0.210 mole) of 2,3-dihydroxypropylamine was added. The mixture was warmed until solution was complete and 0.50 g. of sodium methoxide was added. The reaction mixture was heated at reflux (108° C.) for two hours. The resulting solution was cooled to 50° C., ethanol added to provide a total volume of 300 ml., the mixture warmed to 60° C. and 1.0 g. of 10% palladium-on-carbon catalyst was added. The reaction mixture was hydrogenated on a Parr shaker for two hours after which time hydrogenation was complete. The catalyst was removed by filtration and the filtrate made strongly acid with ethanolic hydrogen chloride. The product which crystallized from solution was collected, washed with ethanol and ether and air dried to give 34.0 g. (93.7%) of the hydrochloride salt of 5-amino-N,N'-bis(2,3-dihydroxypropyl)isophthalamide, m.p. 217–220° C.

EXAMPLE 2

To 800 ml. of 2-methoxyethanol, stirred under nitrogen, was added 1 g. of sodium metal. Stirring was continued at ambient temperature until the sodium had completely dissolved. The nitrogen was turned off and the reaction vessel charged with 191.1 g. (2.100 moles) of 2,3-dihydroxypropylamine of 97% purity and 239.0 g. (1.000 mole) of dimethyl 5-nitroisophthalate. The reaction mixture was heated at reflux (108° C.) for three hours at which time thin layer chromatography indicated only a trace of monoamide. The hot reaction mixture was charged into a 2 liter Parr bottle and washed in with 2-methoxyethanol. About 100 ml. of additional 2-methoxyethanol was added to bring the Parr bottle to its 1200 ml. operating volume, the bottle was flushed with nitrogen, and 5.0 g. of 10% palladium-on-carbon catalyst was added. The bottle containing the mixture was placed on a shaker under hydrogen while maintaining the mixture at about 60° C. Uptake of hydrogen ceased after 2.5 hours, and the catalyst was removed by filtration and washed with 300 ml. of ethanol. To the light amber filtrate was added a large excess of ethanolic hydrogen chloride, and the product which crystallized was cooled and collected by filtration. The filter cake was washed with 400 ml. of ethanol and dried at 60° C. for 20 hours to give 357.0 g. (98.3%) of the hydrochloride salt of 5-amino-N,N'-bis(2,3-dihydroxypropyl)-isophthalamide, m.p. 216–220° C.

When the foregoing experiment was carried out under identical conditions but without base catalysis it required 10–12 hours to complete the amide formation. The yield was 95% and the quality of product the same.

An aqueous solution of 5-amino-N,N'-bis(2,3-dihydroxypropyl)isophthalamide hydrochloride was iodinated with sodium iodine dichloride to give 5-amino-2,4,6-triiodo-N,N'-bis(2,3-hydroxypropyl)isophthalamide in 73–81% crude yield (66–71% purified yield).

EXAMPLE 3

A 12 liter flask was charged with 8 liters of 2-methoxyethanol and the system blanketed with nitrogen. Sodium metal (86 g.) was added in small pieces over 45 minutes, allowing the temperature to rise from 25° C. to 55° C. The mixture was stirred until the sodium had completely dissolved to form a catalyst solution for the following reaction.

A 50 gallon glass-lined reactor was charged with 20.5 kg. (85.7 moles) of dimethyl 5-nitroisophthalate (m.p. 122–124° C.), 16.4 kg. of 2,3-dihydroxypropylamine, 64 liters of 2-methoxyethanol and the catalyst solution obtained above. The reaction mixture was stirred at reflux (108° C.) for four hours at which point thin layer chromatography showed that no starting ester was present. The resulting solution of nitro bis-amide was cooled at ambient temperature and transferred to a 50 gallon hydrogenator to which 325 g. of 10% palladium-on-carbon catalyst was then added. Hydrogenation started at 36° C. and was complete in about one hour with an exothermic effect, the temperature reaching a maximum of 106° C. The reaction mixture was stirred for an additional hour, the catalyst filtered off, and the unit and filter washed with an additional 32 liters of 2-methoxyethanol. The resulting solution was cooled to 25° C. and ethanolic hydrogen chloride (5 kg. of anhydrous hydrogen chloride in 24 liters of ethanol) was added. The system was cooled to 0° C. with stirring and the crystalline material which separated was collected by filtration, washed with 64 liters of cold ethanol and dried in vacuo at 60° C. for 24 hours to afford 30.2 kg. (96.9%) of the hydrochloride salt of 5-amino-N,N'-bis-(2,3-dihydroxypropyl) isophthalamide, m.p. 211–214° C. A duplicate run gave a 99.6% yield of product. Thin layer chromatographic analysis indicated that the product was over 99% pure containing small traces of inorganic salts which could readily be removed by slurry in methanol.

By replacement of the 2,3-dihydroxypropylamine in the foregoing preparation by an equal amount of 1,3-dihydroxy-2-propylamine and following exactly the same procedure it is contemplated that 5-amino-N,N'-bis(1,3-dihydroxy-2-propyl)isophthalamide or an acid-addition salt thereof can be prepared in yield comparable to that realized for the isomeric compound.

What is claimed is:

1. The process for preparing a compound of the formula

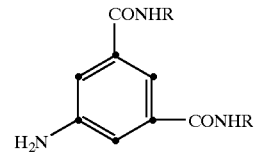

where R is $CH_2CH(OH)CH_2OH$ or $CH(CH_2OH)_2$, which comprises reacting a di-lower-alkyl 5-nitroisophthalate with at least two molar equivalents of a compound of the formula $RNH_2$ in a solvent comprising a lower-aliphatic alcohol containing a basic catalyst to obtain a solution containing 5-nitro-N,N'-bis(R)isophthalamide, and, without isolating the latter, catalytically hydrogenating said solution to obtain a solution of 5-amino-N,N'-bis(R)isophthalamide.

2. The process according to claim 1 in which the 5-amino-N,N'-bis(R)isophthalamide is subsequently isolated either in the form of the free base or an acid-addition salt.

3. The process according to claim 1 wherein the base catalysis is provided by the addition of a solution derived from dissolving metallic sodium in a lower-aliphatic alcohol.

4. The process according to claim 1 wherein the lower-aliphatic alcohol is 2-methoxyethanol.

5. The process according to claim 1 wherein R is $CH_2CH(OH)CH_2OH$ and the di-lower-alkyl 5-nitroisophthalate is dimethyl 5-nitroisophthalate.

6. The process for preparing 5-amino-N,N'-bis(2,3-dihydroxypropyl)isophthalamide which comprises heating at reflux temperature a solution of dimethyl 5-nitroisophthalate and about 2.1 molar equivalents of 3-amino-1,2-propanediol in 2-methoxyethanol containing a catalytic amount of dissolved sodium until essentially all of the dimethyl 5-nitroisophthalate has been consumed, and hydrogenating said mixture in the presence of a palladium-on-carbon catalyst until reduction of the nitro group to an amino group is essentially complete.

7. The process according to claim 6 in which the 5-amino-N,N'-bis(2,3-dihydroxypropyl)isophthalamide is isolated in the form of its hydrochloride salt by adding hydrogen chloride as a gas or a solution in a lower-alkanol.

* * * * *

UNITED STATES PATENT AND TRADEMARK OFFICE
CERTIFICATE OF CORRECTION

PATENT NO.     : 6,441,235 B1
DATED          : August 27, 2002
INVENTOR(S)    : Edward David Parady and Karl Olaf Gelotte It is certified that error appears in the above-identified patent and that said Letters Patent is hereby corrected as shown below:

<u>Title page,</u>
Item [73], Assignee, "Amersha" should read -- Amersham --

Signed and Sealed this

Fourteenth Day of September, 2004

JON W. DUDAS
*Director of the United States Patent and Trademark Office*